United States Patent [19]

Macri

[11] Patent Number: 5,024,936

[45] Date of Patent: Jun. 18, 1991

[54] ASSESSING FETAL LUNG MATURITY

[76] Inventor: James Macri, 170 Sidney St., Oyster Bay, N.Y. 11771

[21] Appl. No.: 249,326

[22] Filed: Sep. 26, 1988

[51] Int. Cl.$^5$ .............................................. C12Q 1/28
[52] U.S. Cl. ...................................... 435/28; 435/18; 435/19; 435/21; 435/25
[58] Field of Search ............................ 435/19, 25, 28

[56] References Cited

U.S. PATENT DOCUMENTS

| | | | |
|---|---|---|---|
| 4,447,529 | 5/1984 | Greenquist et al. | 435/7 |
| 4,705,753 | 11/1987 | Gregor et al. | 435/180 |
| 4,784,945 | 11/1988 | Artiss | 435/19 |
| 4,800,169 | 1/1989 | Bomer et al. | 435/28 |

OTHER PUBLICATIONS

Muneshige et al.—Chem. Abst., vol. 102 (1985), pp. 200, 511d.
Beutler et al.—Chem. Abst., vol. 99 (1983), pp. 172, 388t.
Muneshige et al.-Chem. Abst., vol. 99 (1983), pp. 172, 177y.
Imamura et al.,—Chem. Abst., vol. 98 (1983), p. 118849f.
Farquharson, "Quantitative Determination of Phosphatidyl Glycerol in Amniotic Fluid by Enzymatic Assay", Clinica Chimica Acta 152, (1985), pp. 55–61.
Bradley et al., "Automated Enzymatic Measurements of Lecithin, Sphingomyelin and Phosphatidyl Glycerol in Amniotic Fluid", Clinical Chemistry, vol. 33, No. 1 (1987), pp. 81–86.

*Primary Examiner*—Sam Rosen
*Attorney, Agent, or Firm*—Kenyon & Kenyon

[57] ABSTRACT

A method for assessing whether the lungs of a fetus are mature comprising obtaining a sample of the amniotic fluid surrounding the fetus and determining the presence or absence of phosphatidyl glycerol in the sample. The presence of phosphatidyl glycerol indicates that the fetus lungs are mature, and the absence indicates that the fetus lungs are not mature. More particularly, in one embodiment of the present invention, the presence of phosphatidyl glycerol is determined by adding phospholipase C to the amniotic fluid to convert the phosphatidyl glycerol to glycerol-3-phosphate. Then adding glycerol-3-phosphate oxidase to convert the glyerol-3-phosphate to dihydroxyacetone phosphate and hydrogen peroxide and then reacting the hydrogen peroxide with a substrate and peroxidase to form a visually detectable reaction product.

4 Claims, 3 Drawing Sheets

ASSESSING FETAL LUNG MATURITY

BACKGROUND OF THE INVENTION

This invention relates to ligand-receptor assays.

Ligand-receptor assay procedures have been known for some time. In such procedures a molecule or substance of interest (ligand) is bound or otherwise reacted with a receptor which is specific to the ligand of interest to form an identifiable or even a quantifiable product.

Often, the receptor is bound to a membrane. Thus, the reaction or binding between the receptor and the ligand of interest is localized at the membrane. When the receptor is bound to a membrane, the sample is allowed to incubate on the surface of the membrane for a sufficient time to allow the ligand to come in contact with and bind or react with the receptor. See, for example, U.S. Pat. No. 4,246,339. Alternatively, an absorbent pad is attached to one side of the membrane to which the receptor is bound. The capillary action of the absorbent pad draws the sample through the membrane and brings the ligand in contact with the receptor. See, for example, U.S. Pat. No. 4,727,019.

While the use of an absorbent backing pad has proven to have practical application, it is not without its limitations and disadvantages. The process can be slow, especially if relatively large samples are used or if the absorbent pad approaches its saturation point, even if only in the area immediately below the membrane. Absorbent pad devices can be impractically bulky if more than a few hundred microliters must be applied to the device. The void volume within the absorbent pad places a practical limitation on the amount of fluid which can be applied to the membrane and be quickly and successfully drawn through by the capillary action of the pad.

It is therefore desired to obtain a membrane bound, ligand-receptor assay system which can draw moderate to large volumes of sample through a membrane to which a receptor is bound. It is also desired that such a system be capable of drawing the sample through the membrane as quickly as possible.

SUMMARY OF THE INVENTION

The present invention provides for a device and method for quickly and effectively performing ligand-receptor assays. According to the invention, a sample is applied to a surface of a membrane to which a receptor which is specific to the ligand of interest has been bound. A vacuum is applied to the membrane which draws the sample through the membrane. By this technique, relatively large volumes of sample can be almost instantaneously drawn through the membrane. It is also possible by this same technique to apply washing and disclosing reagents to the membrane. All of this can be accomplished without the use of bulky absorbent pads.

DETAILED DESCRIPTION OF THE INVENTION

Figure 1:
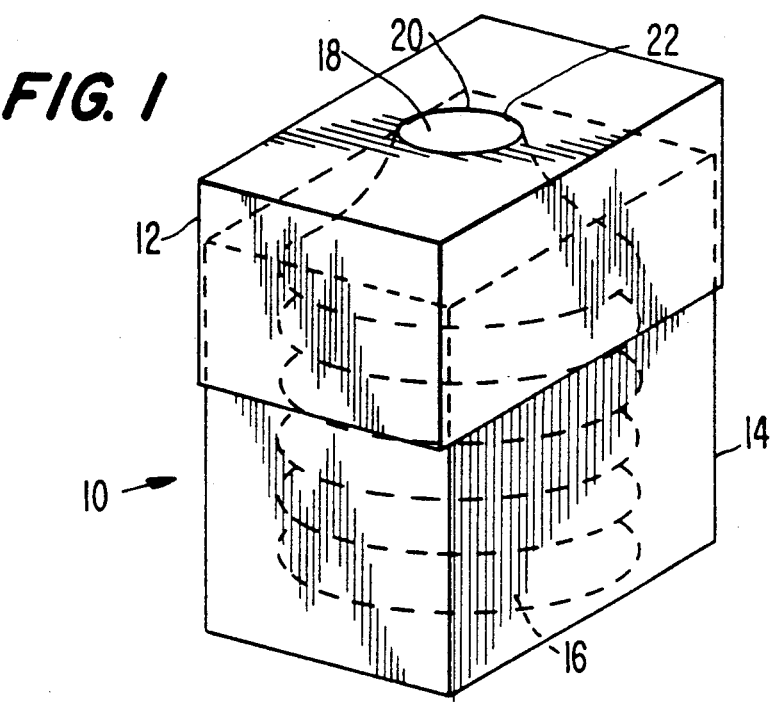

As described above, this invention calls for the use of a membrane to which a receptor which is specific for the ligand of interest has been bound. This membrane must be sufficiently porous to permit the sample fluid (and any other fluids which may be applied to the membrane) to be drawn through the membrane when a vacuum is applied. Any of a variety of known filtering membranes may be used. These membranes may be made from any of a variety of known synthetic or natural materials. A porous nylon membrane is especially useful. Other membranes such as nitrocellulose, zetabind nylon membranes, DEAE cellulose and paper also may be used.

The membrane is typically flexible and must be provided with a support or frame. The nature of the support or frame will in large part, be dictated by the nature of the device which applies the vacuum to the membrane and by the manner in which the membrane is exposed to the sample and other reagents.

The term "receptor", as used in this application, refers to any molecule or substance which is capable of binding or reacting specifically with either the ligand which is the subject of the assay procedure or With characteristic reaction products Which result from reactions involving the ligand of interest. Thus, the identity of the receptor in any given instance will be determined by the identity of the ligand which is the subject of the assay.

One skilled in the art may choose any appropriate receptor molecule without departing from the spirit or scope of this invention. For example, the receptor may be an antibody (monoclonal or polyclonal), an antigen, an anti-antibody, a nucleic acid or an enzyme. Antibodies can be used as receptors in tests for herpes, AIDS, human chorionic gonadotropin, hepatitis, alpha fetoprotein and many other ligands of interest. Membrane bound enzymes can be used in tests for lipids and phospholipids, including cholesterol, triglycerides and phosphatidyl glycerol.

A vacuum is applied to the membrane by a vacuum generating means. The vacuum generating means is affixed to the membrane by any of a variety of sealing devices. These may include O-rings, gaskets and the like. A sealing means may be bound directly to the membrane or may be attached to the frame which supports the membrane. Optionally, the sealing means may serve to either permanently or detachably affix the membrane to the vacuum generating means.

The vacuum generating means which is used in the present invention may be any of a variety of known vacuum generating devices. While mechanical pumps are within the scope of such devices, simpler and less expensive vacuum generating means are preferred.

Generally speaking, a compressible chamber which can be compressed and then expanded is the preferred vacuum generating means. Such a compressable chamber means also serves as a container into which fluids which have been drawn through the membrane can be retained.

The compressible chamber should be constructed so that the difference between its expanded volume and its compressed volume is sufficient to draw the entire sample into the chamber. In devices where the vacuum generating means is also used to draw wash fluids and other reagents through the membrane, the compressed volume of the vacuum generating means should be sufficient to retain both the sample and all subsequently added fluids.

The restoring force which restores the compressible chamber to its expanded volume upon release of the compressing force is important in the construction and operation of this invention. Frequently, it will be advantageous to construct the device so that the chamber exerts its own restoring force or to construct the chamber with a mechanical assist, such as a spring. In any event, the restoring force must not be so great as to render compression of the device difficult but should be sufficiently great to result in efficient expansion of the compressible device from its compressed state upon release of the compressing force so that the entire sample is drawn through the membrane quickly and completely. In some situations it may be desirable to use a compressable chamber which does not exert its own restoring force. Such a device can permit manual expansion of the chamber for a more controlled application of the vacuum force.

FIG. 1 is a view of a preferred vacuum generating means. Vacuum generating means 10 comprises an upper box 12 and a loWer box 14. Upper box 12 nests over lower box 14 and may be raised or lowered along lower box 14. Within the space defined by upper box 12 and lower box 14 is a flexible bellows 16. Flexible bellows 16 has an opening 18 which is affixed to a corresponding aperture 20 in the upper surface of box 12. A sealing means 22 is arranged about the circumference of aperture 20.

In use, upper box 12 is slid down along lower box 14, thereby transmitting a compressing force to bellows 16. Then, a suitably prepared membrane is placed on the sealing means 22 of vacuum generating means 10 creating a sealed relationship between membrane 21 and vacuum generating means 10. While the bellows 16 is maintained in a compressed state, a sample is applied to the membrane. The compressive force on bellows 16 is then released and upper box 12 slides upward along lower box 14. As the bellows expands, suction is created and the sample is drawn within the chamber of flexible bellows 16. Wash solutions and disclosing reagents may be drawn through the membrane in the same manner.

The volume of the chamber within bellows 16 can be sufficiently large so that, even in its fully compressed state, it will contain the entire sample volume, and any subsequent wash solutions or reagents which may be drawn through the membrane. It has been found that by using this procedure, the sample and all of the solutions necessary to carry out the "wet chemistry" of a ligand-receptor assay can be applied to the membrane with surprising speed and ease. A device such as this is capable of drawing moderate to large volumes of fluid through the membrane more quickly than an absorbent pad and can do so without any of the adverse affects which are caused by saturation of the void spaces of an absorbent pad (whether such saturation occurs throughout the absorbent pad or only locally, near the lower surface of the membrane).

Figure 2A:
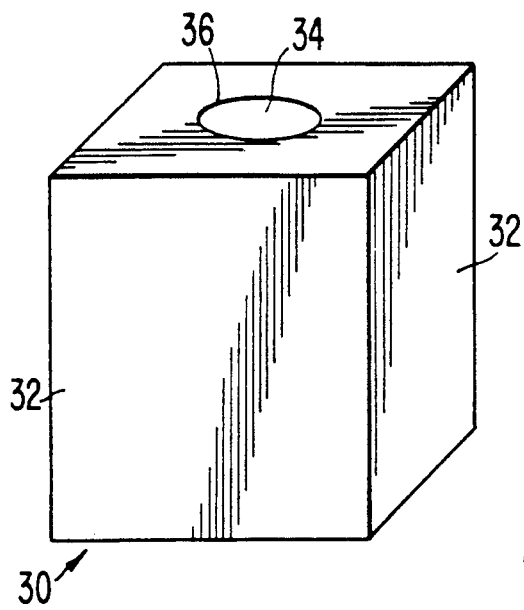
Figure 2B:
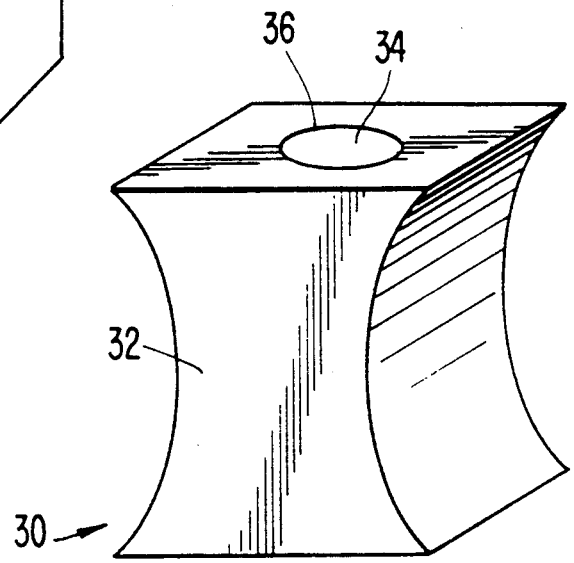

FIGS. 2A and 2B show yet another advantageous arrangement of a vacuum generating means according to the present invention. Vacuum generating means 30 is a cube-shaped device with flexible lateral surfaces 32. Vacuum generating means 30 has an aperture 34 on its upper surface with sealing means 36 about the opening of aperture 34. A membrane can be placed on the upper surface of vacuum generating device 30 in a sealing relationship with sealing means 34. The flexible walls of vacuum generating device 30 can be compressed as is shown in FIG. 2B and a sample added to the membrane. Vacuum generating device 30 can then be allowed to return to its un-compressed state (as in FIG. 2A), thereby creating a vacuum which will quickly and rapidly draw the sample through the membrane and into the chamber defined by cube-shaped vacuum generating means 30.

Figure 3A:
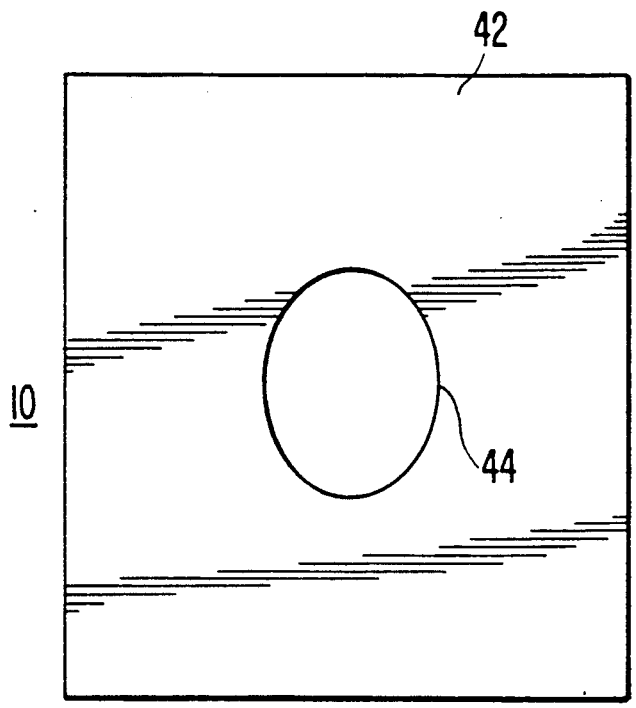
Figure 3B:
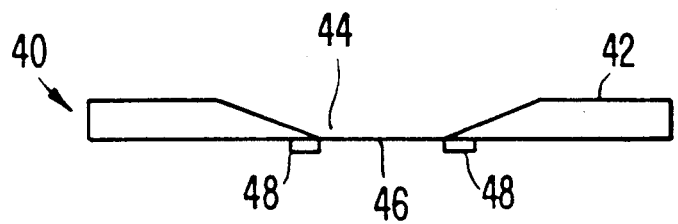

FIG. 3A is a view of the upper surface of a membrane assembly which can be used in connection with the vacuum generating devices shown in FIGS. 1, 2A and 2B. Membrane assembly 40 includes a frame 42 having an aperture 44. A membrane 46 is heat sealed across aperture 44. FIG. 3B is a cross sectional view of membrane assembly 40 through plane A of FIG. 3A. In this view one can see frame 42 and aperture 44 as well as membrane 46 which seals aperture 44. Additionally, sealing ring 48 is located on the lower surface of the frame 42 about the perimeter of aperture 44.

In use, assembly 40 is placed on the upper surface of the vacuum generating means 10 shown in FIG. 1 or means 30 shown in FIGS. 2A & 2B. Sealing ring 48 is placed against sealing means 22 or 34 of the vacuum generating means thereby positioning the membrane 46 above the vacuum generating means in a sealed relationship so that a vacuum may be applied to the lower surface of the membrane 46. Alternatively, sealing ring 48 can be integrally formed with sealing means 22 or 34 to make a unitary structure which includes the vacuum generating means and the membrane assembly.

Figure 4:
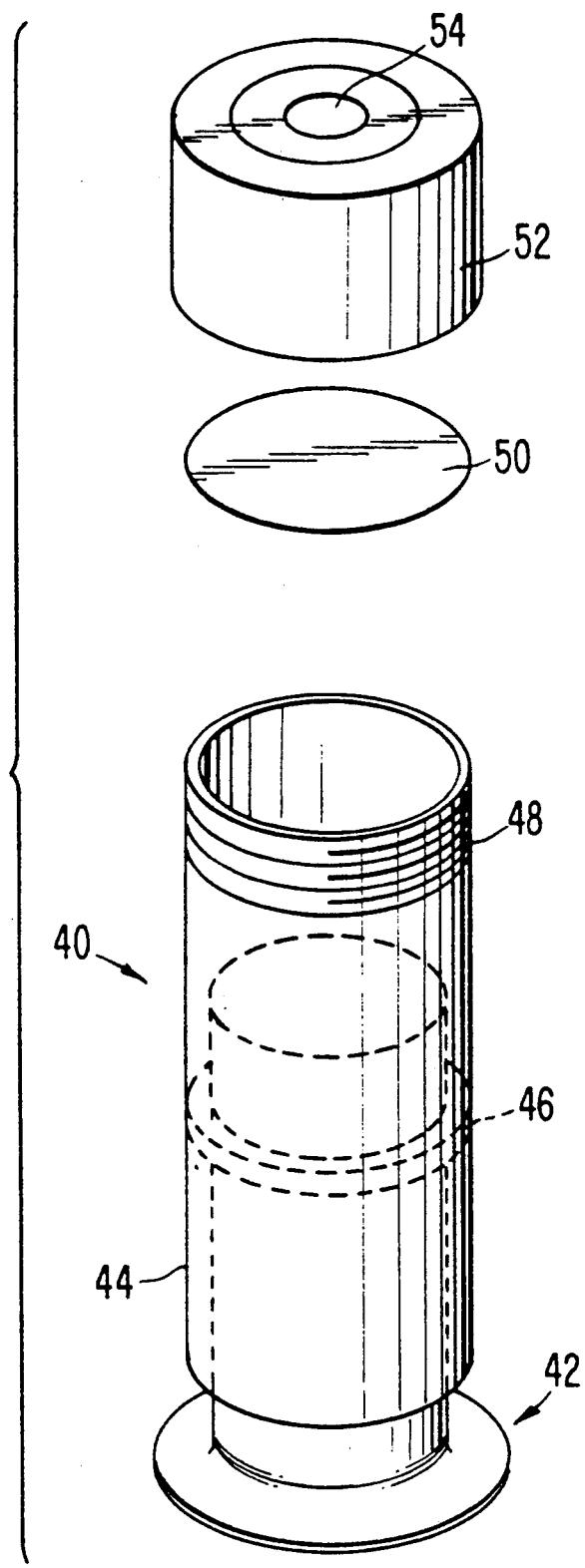

FIG. 4 is an exploded view of another vacuum generating device with a sample membrane.

Device 40 includes a base 42 which fits inside outer casing 44. A water and air tight seal between base 42 and outer casing 44 by an O-ring 46. The upper portion of outer casing 44 includes a threaded section 48 and is adapted to receive a membrane assembly 50. Membrane assembly 50 is sealed over the opening in the outer casing 44 by a threaded screw cap 52 which has a sample opening 54 through which a sample may be applied to the membrane. The base 42 and outer casing 44 define a compressible chamber which can be compressed by pushing the outer casing 44 down along the base 42 and which is expanded by raising the casing 44 along base 42. The casing may be raised either manually or by the action of a spring (not shown) which is coiled about the base 42 to act against the bottom of outer casing 44.

The speed with which a device according to the present invention draws a liquid sample through a suitably prepared membrane was measured by using a commercially available, POREX brand absorbent pad device and a device such as is illustrated in FIG. 1. Normal human serum was used as a liquid sample. The result of this test is set forth in Table 1.

TABLE 1

| Absorption Times for Various Sample Sizes | | | |
|---|---|---|---|
| | 200 l | 1 ml | 2 ml |
| Absorbent Pad | 44 sec | >10 min | inoperable |
| Membrane | 1.9 sec | 10.8 sec | 21.3 sec |
| (All times an average of 4 trials) | | | |

From the foregoing it can be seen that, for fairly small samples, the absorbent pad device was operable, but slower by an order of magnitude than the device of the present invention. For moderate size samples (i.e., one milliliter) the device of the present invention operates quickly and efficiently while the absorbent pad device was barely operable. For relatively large volume samples, the absorbent pad device was inoperable while the device according to the present invention remained efficient and effective.

The use of a device according to the present invention will now be described by way of the following non-limiting examples.

EXAMPLE 1

A membrane assembly as shown in FIG. 3B was constructed using a porous nylon membrane material.

One microliter of a 1.15 mg/ml solution of antibodies to alpha fetoprotein (AFP) was adhered to the membrane which was then allowed to dry and then "blocked" by placing it for 30 minutes in a 10% solution of nonfat dry milk with 0.5% Triton X-100 surfactant added.

The membrane assembly was placed in a sealed relationship on the upper surface of a box-type vacuum generating means such as shown in FIG. 1. The device was compressed, and 50 microliters of serum known to contain 100 IU/ml of AFP was applied to the upper surface of the membrane. The device was then allowed to expand. The resulting vacuum drew the sample through the membrane almost instantaneously. Fifty microliters of a conjugate antibody (AFP antibody conjugated with peroxidase) was then applied to the membrane in the same manner, as were 5 successive washings with 50 microliters of phosphate buffered saline. Finally, 400 microliters of a disclosing reagent (a 0.8 mg/ml solution of o-phenylene diamine) was similarly added to the membrane. Within one minute, a distinct color reaction took place on the surface of the membrane indicating the presence of AFP with no noticeable background coloration.

EXAMPLE 2

Devices according to the present invention have particular utility in procedures which call for the use of larger sample and/or reagent volumes than can be accommodated by an absorbent pad device of practical size. For example, an assay for phosphatidyl glycerol in amniotic fluid, an important indication of fetal lung maturity is preformed as follows, using 5.6 ml of liquid.

An assay for the presence of phosphatidyl glycerol in human amniotic fluid was performed using a device such as was used in Example 1. A five milliliter sample of amniotic fluid was added to a plastic tube. Two hundred microliters of a preparation of phospholipase C (500 IU) was added to the amniotic fluid. The mixture was allowed to incubate for thirty minutes at room temperature. The phosphatidyl glycerol was thus converted into glycerol-3 phosphate and phosphatidic acid. One hundred microliters (20 IU) of glycerol-3-phosphate oxidase was then added to the reaction mixture and incubated for fifteen minutes, thereby converting the glycerol-3-phosphate to dihydroxyacetone phosphate and hydrogen peroxide. Five hundred microliters of tetramethylbenzidene at a concentration of 1 mg/ml was added. The resulting preparation was then drawn through a membrane as in Example 1, the membrane having been previously prepared by binding the enzyme peroxidase to the membrane. By action of the peroxidase, hydrogen peroxide was converted to water and tetramethylbenzidene was converted to an oxidized, colored form. The resulting colored spot on the membrane indicated the presence of phosphatidyl glycerol.

This assay has significant clinical utility. Phosphatidyl glycerol is an indicator of the maturity of the fetal lung. Presence of phosphatidyl glycerol in the amniotic fluid indicates that the fetal lung has attained a level of maturity which is sufficient to enable it to function properly post-partum.

I claim:

1. A method for the determination of whether the lungs of a fetus are mature by testing for the presence of phosphatidyl glycerol in amniotic fluid comprising the steps of:

obtaining a sample of the amniotic fluid surrounding the fetus;

adding phospholipase C to the sample to create a first mixture and to convert phosphatidyl glycerol to glycerol phosphate;

adding glycerol-3-phosphate oxidase to the first mixture to create a second mixture and to convert the glycerol phosphate to dihydroxyacetone phosphate and hydrogen peroxide;

adding a substrate that will react with the dihydroxyacetone phosphate and a peroxidase in a visibly detectable reaction to the second mixture to create a third mixture and to react the substrate with the dihydroxyacetone phosphate;

passing the third mixture through a membrane having peroxidase bound thereto to create a visibly detectable spot on the membrane through the reaction of the peroxidase, the dihydroxyacetone phosphate, the hydrogen peroxide and the substrate; and, detecting the presence or absence of the visibly detectable spot on the membrane, the presence of the visibly detectable spot indicating that the fetal lungs are mature and the absence of the visibly detectable spot indicating that the fetal lungs are not mature.

2. The method of claim 1 wherein the passing the mixture through a membrane further comprises placing a portion of the third mixture on the membrane and passing the mixture through the membrane with a vacuum generating means.

3. The method of claim 1 wherein the passing the mixture through a membrane further comprises placing a portion of the third mixture on an upper surface of the membrane and passing the mixture through the membrane with a compressible chamber.

4. The method of claim 3 wherein the compressible chamber is in a sealed relationship with a lower surface of the membrane and which chamber will compress upon being subjected to a compressive force and will expand upon the release of the compressive force, thereby generating a vacuum at the lower surface of the membrane, said vacuum being sufficient to draw the third mixture through the membrane, and wherein said chamber is compressed prior to placing the third mixture on the upper surface of the membrane.

* * * * *